US009604952B2

(12) United States Patent
Eissenstat et al.

(10) Patent No.: US 9,604,952 B2
(45) Date of Patent: *Mar. 28, 2017

(54) COMPOSITIONS AND METHODS FOR INHIBITING CYTOCHROME P450 2D6

(71) Applicant: Sequoia Pharmaceuticals, Inc., Potomac, MD (US)

(72) Inventors: Michael Eissenstat, Frederick, MD (US); Dehui Duan, Gaithersburg, MD (US); Ji-Hye Kang, Gaithersburg, MD (US)

(73) Assignee: Sequoia Pharmaceuticals, Inc., Potomac, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/446,303

(22) Filed: Jul. 29, 2014

(65) Prior Publication Data

US 2014/0343078 A1    Nov. 20, 2014

Related U.S. Application Data

(63) Continuation of application No. 13/854,648, filed on Apr. 1, 2013, now Pat. No. 8,791,157, which is a continuation of application No. 12/324,507, filed on Nov. 26, 2008, now Pat. No. 8,569,364.

(60) Provisional application No. 60/990,868, filed on Nov. 28, 2007.

(51) Int. Cl.
| C07D 307/79 | (2006.01) |
| A61K 31/485 | (2006.01) |
| C07D 405/12 | (2006.01) |
| A61K 31/443 | (2006.01) |
| A61K 31/497 | (2006.01) |
| A61K 31/444 | (2006.01) |
| A61K 31/4178 | (2006.01) |
| A61K 31/4196 | (2006.01) |
| C07D 471/04 | (2006.01) |
| A61K 31/437 | (2006.01) |
| A61K 31/343 | (2006.01) |
| C07D 405/14 | (2006.01) |
| C12N 9/02 | (2006.01) |
| C07D 407/12 | (2006.01) |

(52) U.S. Cl.
CPC .......... *C07D 307/79* (2013.01); *A61K 31/343* (2013.01); *A61K 31/4178* (2013.01); *A61K 31/4196* (2013.01); *A61K 31/437* (2013.01); *A61K 31/443* (2013.01); *A61K 31/444* (2013.01); *A61K 31/485* (2013.01); *A61K 31/497* (2013.01); *C07D 405/12* (2013.01); *C07D 405/14* (2013.01); *C07D 407/12* (2013.01); *C07D 471/04* (2013.01); *C12N 9/0077* (2013.01); *C12Y 114/14001* (2013.01)

(58) Field of Classification Search
USPC .. 514/255.05, 469, 289, 337, 333, 397, 383, 514/300; 549/471; 546/284.1, 256, 121; 548/311.4, 266.4; 544/405; 435/184
See application file for complete search history.

(56) References Cited

U.S. PATENT DOCUMENTS

| 5,169,860 | A | 12/1992 | Mohamadi et al. |
| 6,319,946 | B1 | 11/2001 | Hale et al. |
| 8,791,157 | B2 * | 7/2014 | Eissenstat ............ C07D 307/79 514/469 |
| 2003/0144220 | A1 | 7/2003 | Obach et al. |
| 2006/0258627 | A1 | 11/2006 | Eissenstat et al. |

FOREIGN PATENT DOCUMENTS

| CA | 2568914 A1 | 12/2005 |
| CN | 1178954 C | 12/2004 |
| CN | 1244575 C | 3/2006 |
| EP | 499299 A2 | 8/1992 |
| EP | 672662 A1 | 9/1995 |
| EP | 1188766 A1 | 3/2002 |
| EP | 1445250 A1 | 8/2004 |
| JP | 11501920 A | 2/1999 |
| JP | 11501921 A | 2/1999 |
| JP | 11503414 A | 3/1999 |
| JP | 2000212182 A | 8/2000 |
| JP | 2001513746 A | 9/2001 |
| JP | 2009525711 A | 7/2009 |
| WO | 9208704 A1 | 5/1992 |
| WO | 9405263 A1 | 3/1994 |
| WO | 9628418 A1 | 9/1996 |
| WO | 9718205 A1 | 5/1997 |
| WO | 9744014 A1 | 11/1997 |

(Continued)

OTHER PUBLICATIONS

Hanna et al.: "Diversity in Mechanisms of Substrate Oxidation by Cytochrome P450 2D6." Journal of Biological Chemistry, Oct. 26, 2001, vol. 276, pp. 39553-39561.
Rowland et al.: "Crystal Structure of Human Cytochrome P450 2D6." Journal of Biological Chemistry, Mar. 17, 2006, vol. 281, pp. 7614-7622.
Shetty et al.: "Tetrahedron Letters", 48(1), 2007, pp. 113-117.
Getman, D., et al.: "Discovery of a Novel Class of Potent HIV-1 Protease Inhibitors Containing the (R)-(Hydroxyethyl)urea Isostere", Journal of Medicinal Chemistry, vol. 36, 1993, pp. 288-291.

(Continued)

*Primary Examiner* — Kristin Vajda
(74) *Attorney, Agent, or Firm* — Edell, Shapiro & Finnan, LLC

(57) ABSTRACT

Methods of inhibiting cytochrome P450 2D6 enzymes are provided that can be used for improving the treatment of diseases by preventing degradation of drugs or other molecules by cytochrome P450 2D6. Pharmaceutical compositions are provided that can act as boosters to improve the pharmacokinetics, enhance the bioavailability, and enhance the therapeutic effect of drugs that undergo in vivo degradation by cytochrome P450 2D6 enzymes.

10 Claims, No Drawings

(56) References Cited

FOREIGN PATENT DOCUMENTS

| WO | 9842318 | A1 | 10/1998 |
|---|---|---|---|
| WO | 2004043903 | A1 | 5/2004 |
| WO | 2004048329 | A1 | 6/2004 |
| WO | 2005092885 | A1 | 10/2005 |
| WO | 2005110428 | A2 | 11/2005 |
| WO | 2006117611 | A1 | 11/2006 |
| WO | 2007111866 | A2 | 10/2007 |
| WO | 2008022345 | A2 | 2/2008 |

OTHER PUBLICATIONS

Krishna, D., et al.: "Extrahepatic Metabolism of Drugs in Humans", Clinical Pharmacokinetic Concepts, 1994, vol. 26, No. 2; pp. 144-160.

Omura, T., et al.: "The Carbon Monoxide-binding Pigment of Liver Microsomes", Journal of Biological Chemistry; vol. 239, No. 7, Jul. 1964, pp. 2370-2378.

Slaughter, R., et al.: "Recent Advances: The Cytochrome P450 Enzymes", The Annals of Pharmacotherapy, vol. 29, Jun. 1995, pp. 619-624.

Getman, D., et al.: "Discovery of a Novel Class of Potent HIV-1 Protease Inhibitors Containing the (R)-(Hydroxyethyl) urea Isostere", Journal of Medicinal Chemistry, 1993, vol. 36, pp. 288-291.

Kane, G., et al.: "Drug-Grapefruit Juice Interactions", Mayo Clinic Proceedings, 2000, vol. 75, pp. 933-942.

Kumar, G. et al.: "Cytochrome P450-Mediated Metabolism of the HIV-1 Protease Inhibitor Ritonavir (ABT-538) in Human Liver Microsomes", Journal of Pharmacology and Experimental Therapeutics, 1996, vol. 277, No. 1, pp. 423-431.

Lee, S., et al.: "Grapefruit juice and its flavonoids inhibit 11B-hydroxysteroid dehydrogenase", Clinical Pharmacology Therapeutics, 1996, vol. 59, pp. 62-71.

Murphy, R. et al.: "Drug Evaluation—Nevirapine: a review of its development, pharmacological profile and potential for clinical use", Expert Opinion Investigative Drugs, 1996, vol. 5, No. 9, pp. 1183-1199.

Waziers, D., et al.: "Cytochrome P 450 Isoenzymes, Epoxide Hydrolase and Glutathione Transferases in Rat and Human Hepatic and Extrahepatic Tissues", Journal of Pharmacology and Experimental Therapeutics, Dec. 7, 1989, vol. 253, No. 1, pp. 387-394.

Zhang, Q., et al.: "Characterization of Human Small Intestinal Cytochromes P-450", American Society for Pharmacology and Experimental Therapeutics, Apr. 7, 1999, vol. 27, No. 7, pp. 804-809.

\* cited by examiner

COMPOSITIONS AND METHODS FOR INHIBITING CYTOCHROME P450 2D6

This application is a continuation of U.S. patent application Ser. No. 13/854,648, filed Apr. 1, 2013, which is a continuation of U.S. patent application Ser. No. 12/324,507, filed Nov. 26, 2008, which claims the benefit of U.S. provisional application Serial No. 60/990,868, filed Nov. 28, 2007, the contents of each of which are herein incorporated by reference in their entirety.

BACKGROUND

Cytochrome P450s (P450) are a family of enzymes involved in the oxidative metabolism of both endogenous and exogenous compounds. P450 2D6 enzymes are widely distributed in the liver, intestines and other tissues (Krishna et al., *Clinical Pharmacokinetics*. 26:144-160, 1994). P450 2D6 enzymes catalyze the phase I reaction of drug metabolism, to generate metabolites for excretion. The classification of P450s is based on homology of the amino acid sequence (Slaughter et al *The Annals of Pharmacotherapy* 29:619-624, 1995). In mammals, there is over 55% homology of the amino acid sequence of CYP450 subfamilies. The differences in amino acid sequence constitute the basis for a classification of the superfamily of cytochrome P450 2D6 enzymes into families, subfamilies and isozymes.

Cytochrome P450 contains an iron cation and is a membrane bound enzyme that can carry out electron transfer and energy transfer. Cytochrome P450, when bound to carbon monoxide (CO), displays a maximum absorbance (peak) at 450 nm in the visible spectra, and is therefore called P450 (Omura et al., *J. Biol. Chem.* 239:2370, 1964).

Over 200 genes encoding cytochrome P450s have been identified, and are divided among over 30 gene families. These gene families are organized into subfamilies, which vary in regulation of gene expression and in amino acid sequence homology, substrate specificity, catalytic activity, and physiological role of the encoded enzymes.

The efficacy of a drug can be dramatically affected by its metabolism in the body. For drugs that are rapidly metabolized it can be difficult to maintain an effective therapeutic dose in the body, and the drug often must be given more frequently, in higher dose, and/or be administered in a sustained release formulation. Moreover, in the case of compounds for treating infectious disease, such as viral or bacterial infections, the inability to maintain an effective therapeutic dose can lead to the infectious agent becoming drug resistant. Many compounds that have strong biological efficacy and that would otherwise be potentially powerful therapeutics are rendered essentially useless by virtue of their short half-lives in vivo. A common pathway of metabolism for drugs is via oxidation by one or more cytochrome P450 2D6 enzymes. These enzymes metabolize a drug to a more polar derivative that is more readily excreted through the kidney or liver. First pass metabolism refers to the elimination of drugs via liver and intestinal CYP450 2D6 enzymes. First pass metabolism can lead to poor drug absorption from the GI tract due to extensive intestinal CYP450 metabolism, low plasma blood levels due to hepatic CYP450 metabolism, or both. Poor oral bioavailability due to CYP450 metabolism is a major reason for the failure of drug candidates in clinical trials. In some instances, metabolic by-products of CYP450 2D6 enzymes are highly toxic and can result in severe side effects, cancer, and even death.

Some examples of drugs affected by CYP450 2D6 enzymes includes antidepressants (imipramine, clomipramine, desimpramine), antipsychotics (haloperidol, perphenazine, risperidone, thioridazine), beta blockers (carvedilol, S-metoprolol, propafenone, timolol), amphetamine, codeine, dextromethorphan, fluoxetine, S-mexiletine, phenacetin, propranolol.

Some examples of the effects of drug metabolism by CYP450 2D6 include

Dextromethorphan: CYP2D6 metabolizes dextromethrophan to dextrorphan. Individuals who express high levels of CYP2D6 (so-called rapid metabolizers) do not receive therapeutic benefits from dextromethorphan due to extensive first-pass metabolism and rapid systemic clearance.

Protease Inhibitors: Protease inhibitors and non-nucleoside reverse transcriptase inhibitors currently indicated for use in treatment of HIV or HCV are typically good substrates of cytochrome P450 2D6 enzymes; in particular, they are metabolized by CYP3A4 enzymes (see e.g. Sahai, AIDS 10 Suppl 1:S21-5, 1996) with possible participation by CYP2D6 enzymes (Kumar et al., *J. Pharmacol. Exp. Ther.* 277(1):423-31, 1996). Although protease inhibitors are reported to be inhibitors of CYP3A4, some non-nucleoside reverse transcriptase inhibitors, such as nevirapine and efavirenz, are inducers of CYP3A4 (see e.g. Murphy et al., *Expert Opin Invest Drugs* 5/9: 1183-99, 1996).

Human CYP450 isozymes are widely distributed among tissues and organs (Zhang et al., *Drug Metabolism and Disposition*. 27:804-809, 1999). With the exception of CYP1A1 and CYP2A13, most human CYP450 isozymes are located in the liver, but are expressed at different levels (Waziers J. Pharmacol. Exp. Ther. 253: 387, 1990). A solution to the problem of drug degradation and first-pass metabolism is to control the rate of drug metabolism. When the rates of drug absorption and metabolism reach a steady state, a maintenance dose can be delivered to achieve a desired drug concentration that is required for drug efficacy. Certain natural products have been shown to increase bioavailability of a drug. For example, the effect of grapefruit juice on drug pharmacokinetics is well known. See Edgar et al., Eur. J. Clin. Pharmacol. 42:313, (1992); Lee et al., Clin. Pharmacol. Ther. 59:62, (1996); Kane et al., Mayo Clinic Proc. 75:933, (2000). This effect of grapefruit juice is due to the presence of natural P450-inhibiting components. Other compounds also have been used for inhibition of P450. For example, the HIV-1 protease inhibitor Ritonavir® is now more commonly prescribed for use in combination with other, more effective, HIV protease inhibitors because of its ability to "boost" those other compounds by inhibiting P450-mediated degradation.

SUMMARY OF THE INVENTION

Compounds and methods of inhibiting cytochrome P450 2D6 enzymes are provided. Also provided are methods of enhancing the therapeutic effect of drugs that are metabolized by cytochrome P450 2D6 enzymes, methods of decreasing the toxic effects of drugs that are metabolized to toxic by-products by cytochrome P450 2D6 enzymes, methods of increasing oral bioavailability of drugs that are metabolized by cytochrome P450 2D6 enzymes, and methods of curing diseases that are caused or exacerbated by the activity of cytochrome P450 2D6 enzymes.

An advantage of the invention is that it provides improved inhibitors of cytochrome P450 2D6 enzymes. Another advantage is that it provides a method of controlling the pharmacokinetic properties of drugs. Another advantage is that it helps control the rate of metabolism of drugs. Another advantage is that it controls the degradation of drugs. Another advantage is that it enhances the bioavailability of drugs. Another advantage is that it enhances the efficacy of drugs. Another advantage is that it boosts the efficacy of certain drugs so that the drugs can be administered at a lower concentration or dosage thereby reducing their toxicity. Another advantage is that these properties can lower the overall cost associated with the treatment of disorders.

More particularly, in one aspect, there is provided a compound represented by a formula:

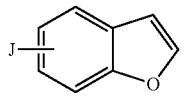

where J includes a basic amino group and 1 to 8 carbon atoms optionally containing from 1 to 3 heteroatoms independently selected from the group consisting of O, S, and N; or a salt form thereof; and where the compound inhibits cytochrome P450 2D6 enzyme.

In another aspect, there is provided a method of inhibiting cytochrome P450 2D6 enzyme including administering to a patient a compound including a benzofuran moiety attached on its benzene ring via a linker to a basic amino group or a salt form thereof.

In yet another aspect, there is provided a pharmaceutical formulation including a pharmaceutically acceptable diluent, adjuvant or excipient, and a therapeutically effective amount of a compound including a benzofuran moiety attached on its benzene ring via a linker to a basic amino group or a salt form thereof.

In various examples, any of the aspects above or any of the methods or systems or modules described herein, can include one or more of the following features.

In one embodiment, there is provided compound represented by the formula:

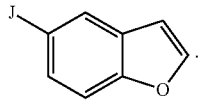

In some embodiments, there is provided the compound where J includes:
J'-N(D)-SO$_n$—, J'-N(D)-CO$_n$—, J'-N(D)-(R)$_q$—, or J'-N(D)-(R)$_q$—; where
n=1-2;
q=0-1;
D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R)-alkyl, N(R)-cycloalkyl, N(R)-cycloalkylalkyl, N(R)-heterocycloalkyl, N(R)-heterocycloalklalkyl, N(R)-heteroaralkyl, N(R)-aralkyl, where D optionally is substituted by alkyl, halo, nitro, cyano, O-alkyl, or S-alkyl; J'is selected from acyl, sulfono, aminoalkyl, arylaminoalkyl, heteroarylaminoalkyl, aralkylaminoalkyl, heteroaralkylaminoalkyl, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R)-alkyl, N(R)-cycloalkyl, N(R)-cycloalkylalkyl, N(R)-heterocycloalkyl, N(R)-heterocycloalkylalkyl, N(R)-heteroaralkyl, N(R)-aralkyl, each of the substituents optionally substituted by alkyl, halo, nitro, cyano, O-alkyl, or S-alkyl; and R is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl.

In some embodiments, D is hydrogen, where R is alkyl and q=1, where J includes J'-N(D)-SO$_2$—, where J includes J'-N(D)-CO-, where R is CH2 and q=1, where J' is aminoalkyl, where J' is arylaminoalkyl, where J' is heteroarylaminoalkyl, where J' is aralkylaminoalkyl, where J' is heteroaralkylaminoalkyl, where J includes an —NH— group or a salt form thereof.

In certain embodiments, the compound can include any combination of the above groups.

There also is provided a compound having the structure:

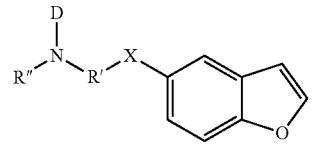

where X is [—N(D)-SO$_n$—]$_q$, where n is 1 or 2 and q is 0 or 1; R' may be $C_1$-$C_6$ alkyl when q is 0, or $C_2$-$C_6$ alkyl when q is 1, where R' optionally is substituted by up to 3 substituents independently selected from the group consisting of $C_1$-$C_3$ alkyl, OH, O-alkyl, alkylamido, alkylcarbamoyl, halo, nitro, cyano, S-alkyl, aralkyl and heteroaralkyl; each D independently may be is selected from the group consisting of hydrogen, alkyl, cycloalkyl, cycloalkylalkyl, heterocycloalkyl, heterocycloalkylalkyl, aryl, heteroaryl, heteroaralkyl and aralkyl; R" is $C_1$-$C_6$ alkyl, $C_3$-$C_6$ cycloalkyl, $C_3$-$C_6$ cycloalkyl-$C_1$-$C_6$-alkyl, heterocycloalkyl, heterocycloalkylalkyl, aryl, heteroaryl, heteroaralkyl or aralkyl, optionally substituted by up to 3 substituents independently selected from the group consisting of OH, O-alkyl, alkylamido, alkylcarbamoyl, halo, nitro, cyano, S-alkyl, aralkyl and heteroaralkyl. In one embodiment q is 0, and R' is methylene. In this embodiment D may be H or heteroaralkyl. and R" may be s heteroaryl, heteroaralkyl, or optionally substituted $C_1$-$C_6$ alkyl. In a specific embodiment, R" may be alkylcarbamoyl substituted $C_1$-$C_6$ alkyl.

In another embodiment, q is 1, D is H or alkyl, and R" may be alkyl. In these methods, the compound may be selected from the group consisting of:

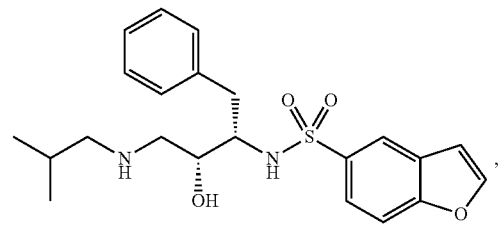

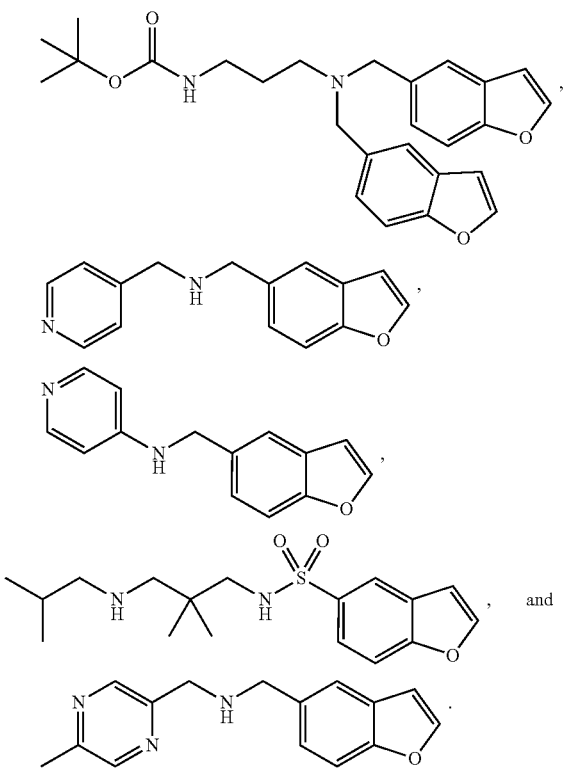

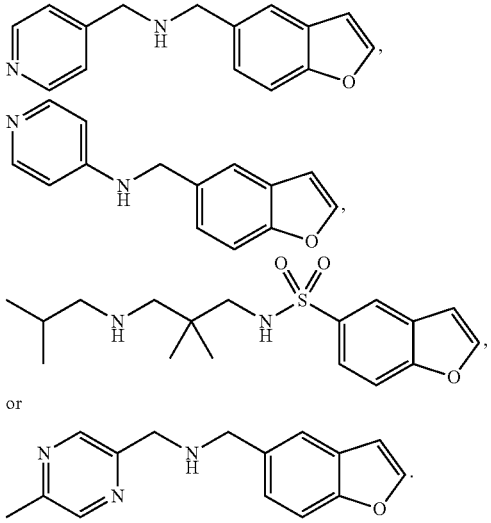

In various embodiments, the linker is at the 5-position of the benzofuran moiety, or where the basic amino group is a secondary or tertiary amine.

In certain embodiments, there is provided a method that can further include administering to a patient a compound represented by a formula:

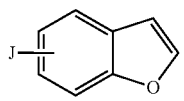

In some embodiments, the compound is selected from:

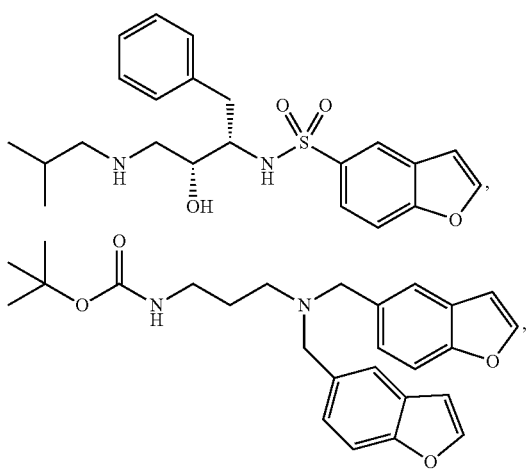

In various embodiments, the method further includes administering the compound prior to or substantially contemporaneously with a drug, where efficacy of the drug is compromised due to degradation by cytochrome P450 2D6 enzyme. The drug may be dextromethorphan. In certain embodiments, there is provided a pharmaceutical formulation where the compound is a cytochrome P450 2D6 inhibitor.

In various embodiments, the pharmaceutical formulation may inhibit the metabolism of dextromethorphan.

In some embodiments, the compound represented by the formula

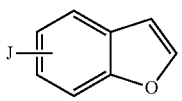

can include:

a group containing from 1 to 12 carbon atoms optionally containing from 1 to 3 heteroatoms independently selected from the group consisting of O, S, and N,
—OCON(R2)—, —S(O)$_n$N(R2)—, —CON(R2)—, —COCO(NR2)—, —N(R2)CON(R2)—, —N(R2)S(O)$_n$N(R2)—, N(R2)CO or —N(R2)COO—;

(CG$_1$G$_2$)$_m$, where m is 0-6 and where G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and where G$_1$ and G$_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties,

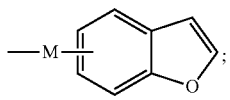

where M is selected from the group consisting of: a bond, $OC(R8)_q$, —CO—, —$SO_n$—, —O—, —O—CO—, —N(D)-$SO_n$—, —N(D)-$CO_n$—, —N(D)-$(R8)_q$-, —$SO_n$—N(D)-$(R8)_q$-, or —$CO_n$—N(D)-$(R8)_q$-, where M can be linked in either orientation with respect to the benzofuran ring, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, where D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, NRS$(O)_nR$, NRC[═N(R)]$N(R)_2$, $N(R)N(R)CO_nR$, $NRPO_nN(R)_2$, $NRPO_nOR$, oxo, ═N—OR, ═N—$N(R)_2$, ═NR, ═NNRC(O)$N(R)_2$, ═NNR$CO_nR$, ═NNRS(O)$_nN(R)_2$, and ═NNRS(O)$_n(R)$;

or each R2 is independently selected from the group consisting of $C_1$-$C_6$ alkyl; substituted by aryl or heteroaryl; which groups optionally are substituted with one or more substituents selected from the group consisting of halo, OR, ROH, R-halo, $NO_2$, CN, $CO_nR$, $CON(R)_2$, C(S)R, C(S)N$(R)_2$, $SO_nN(R)_2$, SR, $SO_nR$, $N(R)_2$, $N(R)CO_nR$, NRS(O)$_nR$, NRC[═N(R)]$N(R)_2$, $N(R)N(R)CO_nR$, $NRPO_nN(R)_2$, $NRPO_nOR$;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, $NO_2$, CN, $CO_nR2$, C(O)N$(R2)_2$, C(O)N(R2)N$(R2)_2$, C(S)R2, C(S)N$(R2)_2$, S(O)$_nN(R2)_2$, SR2, $SO_nR2$, $N(R)_2$, N(R2)$CO_nR2$, NR2S(O)$_nR2$, NR2C[═N(R2)]N$(R2)_2$, N(R2)N(R2)$CO_nR2$, oxo, ═N—OR2, ═N—N$(R2)_2$, ═NR2, ═NNRC(O)$N(R2)_2$, ═NNR2C(O)$_nR2$, ═NNR2S(O)$_nN(R2)_2$, and ═NNR2S(O)$_n(R2)$;

R6 is aryl or heteroaryl, where the aryl or heteroaryl optionally are substituted with one or more groups selected from the group consisting of aryl, heteroaryl, R2, R3, halo, OR2, R2OH, R2-halo, $NO_2$, CN, $CO_nR2$, C(O)N$(R2)_2$, C(O)N(R2)N$(R2)_2$, C(S)R2, C(S)N$(R2)_2$, S(O)$_nN(R2)_2$, SR2, $SO_nR2$, $N(R)_2$, N(R2)$CO_nR2$, NR2S(O)$_nR2$, NR2C[═N(R2)]N$(R2)_2$, N(R2)N(R2)$CO_nR2$, OC(O)R2, OC(S)R2, OC(O)N$(R2)_2$, and OC(S)N$(R2)_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, NRS$(O)_nR$, NRC[═N(R)]$N(R)_2$, $N(R)N(R)CO_nR$, $NRPO_nN(R)_2$, $NRPO_nOR$, oxo, ═N—OR, ═N—$N(R)_2$, ═NR, ═NNRC(O)$N(R)_2$, ═NNR$CO_nR$, ═NNRS(O)$_nN(R)_2$, and ═NNRS(O)$_n(R)$;

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and q=0-1, where the benzene ring of the benzofuran moiety may optionally by substituted by up to three substituents independently selected from the group consisting of R2, halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, NRS$(O)_nR$, NRC[═N(R)]$N(R)_2$, $N(R)N(R)CO_nR$, $NRPO_nN(R)_2$, and $NRPO_nOR$, where the up to three substituents do not form a ring between any adjacent carbon atoms of the benzene ring, and with the proviso that the compound does not contain a basic aliphatic amine function and does not contain a carboxylic acid group.

In the methods described above, the cytochrome P450 monooxygenase may be CYP2D6.

In specific embodiments, the patient may be suffering from chronic pain, depression, epilepsy, psychosis, inflammation, cancer, cardiovascular disease, diabetes, and/or infection, for example, infection with a hepatitis-causing virus or HIV.

In other embodiments, the compound is administered substantially contemporaneously with a drug where efficacy of the drug is compromised due to degradation by cytochrome P450 2D6.

The details of one or more examples are set forth in the accompanying reaction schemes and description. Further features, aspects, and advantages of the invention will become apparent from the description, the schemes, and the claims.

DETAILED DESCRIPTION

Compounds and method for inhibiting cytochrome P450 2D6 enzymes are provided. More particularly, methods are provided for enhancing the therapeutic effect of drugs in which the efficacy is compromised due to degradation mediated by cytochrome P450. The methods include administering compounds or pharmaceutical compositions containing the compounds in any therapeutic regimen where one or more primary drugs is metabolized by a CYP. The compounds or pharmaceutical compositions can be administered when the primary drug either becomes inactive or is converted to a toxic metabolite due to metabolism by a CYP. The compounds or compositions can inhibit or reduce the rate of degradation of drugs that are effective against a variety of diseases and that are degraded by cytochrome P450 2D6 enzymes. Upon co-administration, the compounds and compositions can, for example, maintain intracellular concentrations of the drugs at a therapeutic level for a sustained period of time. The methods are useful, for example, in treating a variety of disorders such as, cardiac arrhythmia, depression, psychosis, chronic pain, and infections such as HIV or HCV. The compounds or compositions can be administered either alone or in combination with drugs such as analgesics, anti-depressants, anti-psychotics, antibiotics, anti-arrythmics, steroids, anesthetics, muscle relaxants, cardiac stimulants, NSAIDs, anti-epileptics, or protease inhibitors, such as HIV or HCV protease inhibitors.

In particular, there is provided a method of inhibiting cytochrome P450 2D6 enzyme by administering to a patient, a compound represented by a formula:

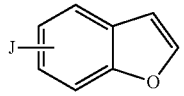

where J includes a basic amino group and 1 to 8 carbon atoms optionally containing from 1 to 3 heteroatoms independently selected from the group consisting of O, S, and N; or a salt form thereof; and where the compound inhibits cytochrome P450 2D6 enzyme.

In one embodiment, the compound may be represented by the formula:

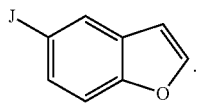

In some embodiments, J may include:
J'-N(D)-SO$_n$—, J'-N-CO$_n$—, J'-N-(R)$_q$—, or J'-N(D)-(R)$_q$—; where
n=1–2;
q=0–1;
D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R)-alkyl, N(R)-cycloalkyl, N(R)-cycloalkylalkyl, N(R)-heterocycloalkyl, N(R)-heterocycloalkylalkyl, N(R)-heteroaralkyl, N(R)-aralkyl, where D optionally is substituted by alkyl, halo, nitro, cyano, 0-alkyl, or S-alkyl;
J' is selected from acyl, sulfono, aminoalkyl, arylaminoalkyl, heteroarylaminoalkyl, aralkylaminoalkyl, heteroaralkylaminoalkyl, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R)-alkyl, N(R)-cycloalkyl, N(R)-cycloalkylalkyl, N(R)-heterocycloalkyl, N(R)-heterocycloalkylalkyl, N(R)-heteroaralkyl, N(R)-aralkyl, each of the substituents optionally substituted by alkyl, halo, nitro, cyano, O-alkyl, or S-alkyl; and
R is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl.

In some embodiments, D is hydrogen, where R is alkyl and q=1, where J includes J'-N(D)-SO$_2$—, where J includes J'—N(D)-CO—, where R is CH2 and q=1, where J' is aminoalkyl, where J' is arylaminoalkyl, where J' is heteroarylaminoalkyl, where is aralkylaminoalkyl, where J' is heteroaralkylaminoalkyl, where J includes an —NH— group or a salt form thereof.

In certain embodiments, the compound may include any combination of the above groups.

There also is provided a compound having the structure:

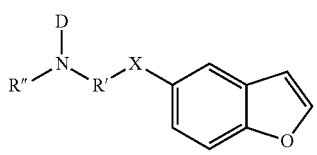

where: X is [—N-SO$_n$—]$_q$, where n is 1 or 2 and q is 0 or 1;
R' may be C$_1$-C$_6$ alkyl when q is 0, or C$_2$-C$_6$ alkyl when q is 1, where R' optionally is substituted by up to 3 substituents independently selected from the group consisting of C$_1$-C$_3$ alkyl, OH, O-alkyl, alkylamido, alkylcarbamoyl, halo, nitro, cyano, S-alkyl, aralkyl and heteroaralkyl;
each D independently may be is selected from the group consisting of hydrogen, alkyl, cycloalkyl, cycloalkylalkyl, heterocycloalkyl, heterocycloalkylalkyl, aryl, heteroaryl, heteroaralkyl and aralkyl;
R" is C$_1$-C$_6$ alkyl, C$_3$-C$_6$ cycloalkyl, C$_3$-C$_6$ cycloalkyl-C$_1$-C$_6$-alkyl, heterocycloalkyl, heterocycloalkylalkyl, aryl, heteroaryl, heteroaralkyl or aralkyl, optionally substituted by up to 3 substituents independently selected from the group consisting of OH, O-alkyl, alkylamido, alkylcarbamoyl, halo, nitro, cyano, S-alkyl, aralkyl and heteroaralkyl.

In specific embodiments q is 0, and R' is methylene; D may be H or heteroaralkyl. and R" may be s heteroaryl, heteroaralkyl, or optionally substituted C$_1$-C$_6$ alkyl. In a specific embodiment, R" may be alkylcarbamoyl substituted C$_1$-C$_6$ alkyl.

In another embodiment, q is 1, D is H or alkyl, and R" may be alkyl. In these methods, the compound may be selected from the group consisting of:

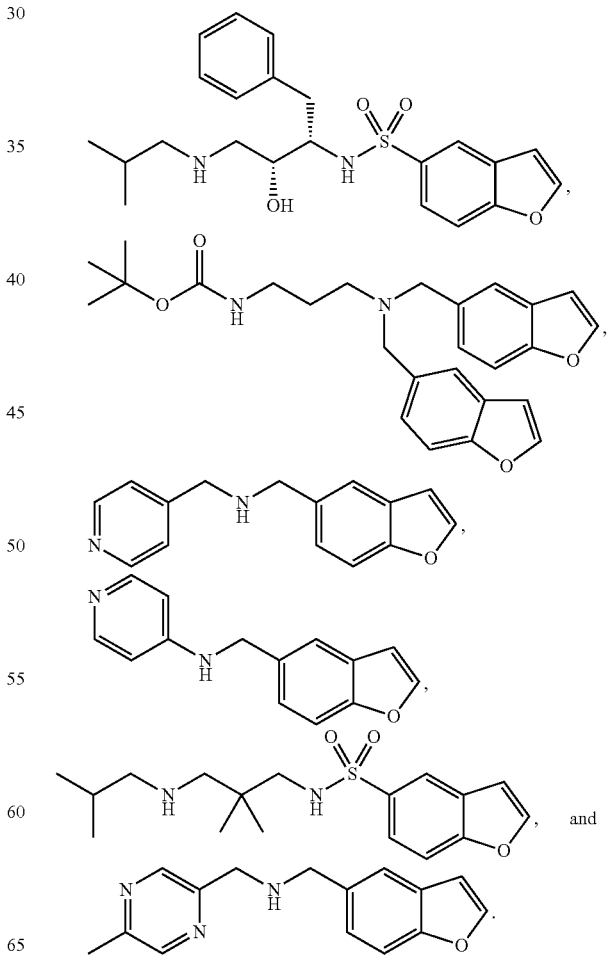

In one aspect, there are provided methods of inhibiting cytochrome P450 2D6 enzyme including administering to a patient a compound including a benzofuran moiety attached on its benzene ring via a linker to a basic amino group or a salt form thereof.

In various embodiments, the linker is at the 5-position of the benzofuran moiety, or where the basic amino group is a secondary or tertiary amine.

In certain embodiments, the method may further include administering to a patient a compound represented by a formula:

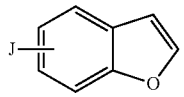

In some embodiments, the the compound is selected from:

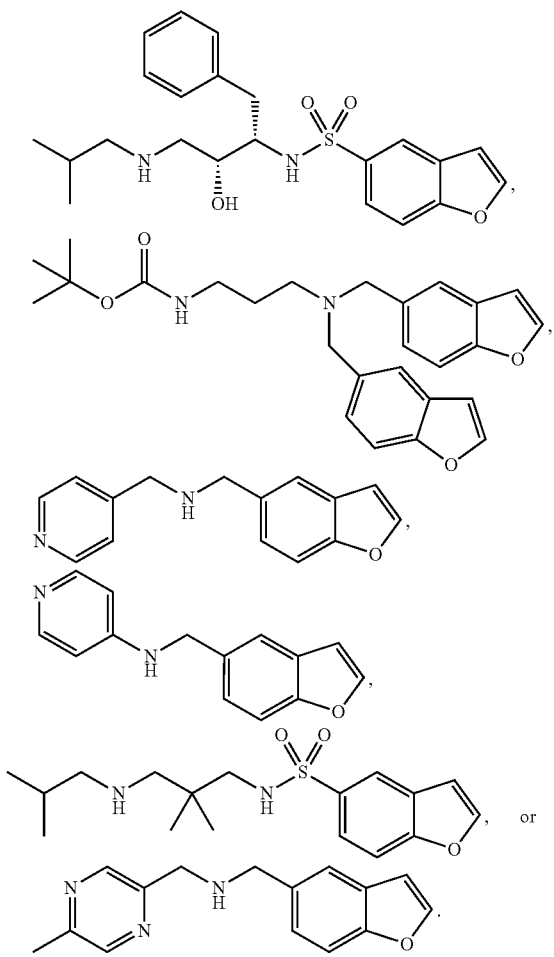

In various embodiments, there are provided methods further including administering the compound prior to or substantially contemporaneously with a drug, where efficacy of the drug is compromised due to degradation by cytochrome P450 2D6 enzyme.

In certain embodiments, the drug whose metabolism is inhibited is dextromethorphan.

In another aspect, there is provided a pharmaceutical formulation including a pharmaceutically acceptable diluent, adjuvant or excipient, and a therapeutically effective amount of a compound including a benzofuran moiety attached on its benzene ring via a linker to a basic amino group or a salt form thereof.

In certain embodiments, the compound is a cytochrome P450 2D6 inhibitor.

In various embodiments, there is provided a pharmaceutical formulation where the compound inhibits the metabolism of dextromethorphan.

In some embodiments, the compound represented by the formula

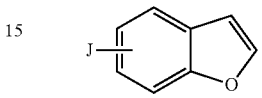

can include:

a group containing from 1 to 12 carbon atoms optionally containing from 1 to 3 heteroatoms independently selected from the group consisting of O, S, and N, —OCON(R2)-, —S(O)$_n$N(R2)-, —CON(R2)-, —COCO (NR2),—N(R2)CON(R2)—, —N(R2)S(O)$_n$N(R2)-, N(R2) CO or —N(R2)COO—;

—(CG$_1$G$_2$)$_m$-, where m is 0-6 and where G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and where G$_1$ and G$_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties,

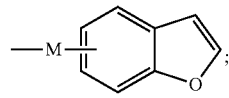

where M is selected from the group consisting of: a bond, OC(R8)$_q$, —CO—, —S$_n$—, —O—, —O—CO—, —N(D)-SO$_n$—, —N(D)-CO$_n$—, —N(D)-(R8)$_q$-, —SO$_n$—N(D)-(R8)$_q$-, or —CO$_n$—N(D)-(R8)$_q$-, where M can be linked in either orientation with respect to the benzofuran ring, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, where D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, $=N-OR$, $=N-N(R)_2$, $=NR$, $=NNRC(O)N(R)_2$, $=NNRCO_nR$, $=NNRS(O)_nN(R)_2$, and $=NNRS(O)_n(R)$;

or each R2 is independently selected from the group consisting of $C_1$-$C_6$ alkyl; substituted by aryl or heteroaryl; which groups optionally are substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, $NO_2$, CN, $CO_nR2$, $C(O)N(R2)_2$, $C(O)N(R2)N(R2)_2$, $C(S)R2$, $C(S)N(R2)_2$, $S(O)_nN(R2)_2$, SR2, $SO_nR2$, $N(R)_2$, $N(R2)CO_nR2$, $NR2S(O)_nR2$, $NR2C[=N(R2)]N(R2)_2$, $N(R2)N(R2)CO_nR2$, oxo, $=N-OR2$, $=N-N(R2)_2$, $=NR2$, $=NNRC(O)N(R2)_2$, $=NNR2C(O)_nR2$, $=NNR2S(O)_nN(R2)_2$, and $=NNR2S(O)_n(R2)$;

R6 is aryl or heteroaryl, where the aryl or heteroaryl optionally are substituted with one or more groups selected from the group consisting of aryl, heteroaryl, R2, R3, halo, OR2, R2OH, R2-halo, $NO_2$, CN, $CO_nR2$, $C(O)N(R2)_2$, $C(O)N(R2)N(R2)_2$, $C(S)R2$, $C(S)N(R2)_2$, $S(O)_nN(R2)_2$, SR2, $SO_4R2$, $N(R)_2$, $N(R2)CO_nR2$, $NR2S(O)_nR2$, $NR2C[=N(R2)]N(R2)_2$, $N(R2)N(R2)CO_nR2$, OC(O)R2, OC(S)R2, $OC(O)N(R2)_2$, and $OC(S)N(R2)_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, $=N-OR$, $=N-N(R)_2$, $=NR$, $=NNRC(O)N(R)_2$, $=NNRCO_nR$, $=NNRS(O)_nN(R)_2$, and $=NNRS(O)_n(R)$;

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and q=0-1, where the benzene ring of the benzofuran moiety may optionally by substituted by up to three substituents independently selected from the group consisting of R2, halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, and $NRPO_nOR$, where the up to three substituents do not form a ring between any adjacent carbon atoms of the benzene ring, and with the proviso that the compound does not contain a basic aliphatic amine function and does not contain a carboxylic acid group.

In specific embodiments, the patient may be suffering from chronic pain, depression, epilepsy, psychosis, inflammation, cancer, cardiovascular disease, diabetes, and/or infection, for example, infection with a hepatitis-causing virus or HIV.

In other embodiments, the compound is administered substantially contemporaneously with a drug where efficacy of the drug is compromised due to degradation by cytochrome P450 monooxygenase.

An exemplary and non-limiting group of compounds that can act as cytochrome P450 2D6 enzyme inhibitors is illustrated by the following compounds are:

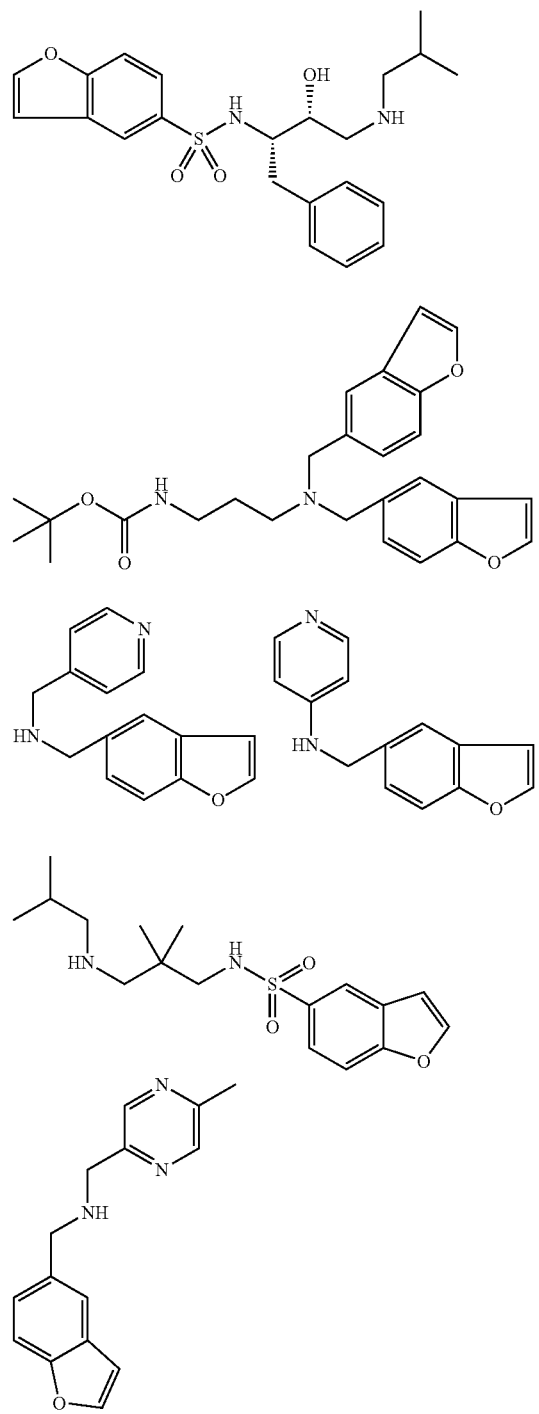

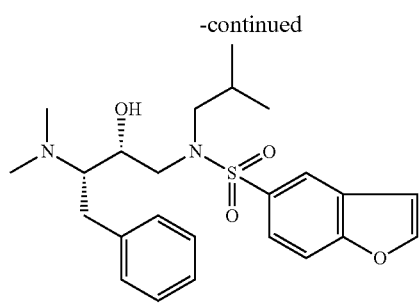
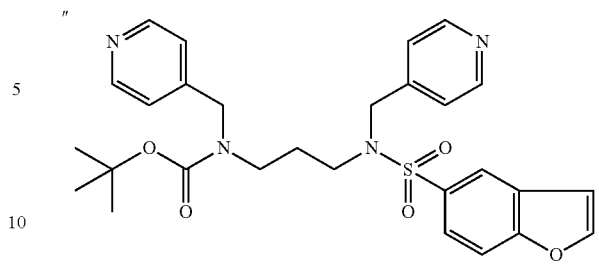
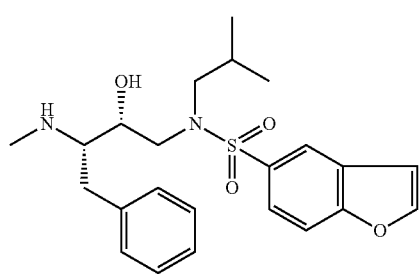 [SMILES: CN[C@@H](Cc1ccccc1)[C@H](O)CN(CC(C)C)S(=O)(=O)c1ccc2occc2c1]
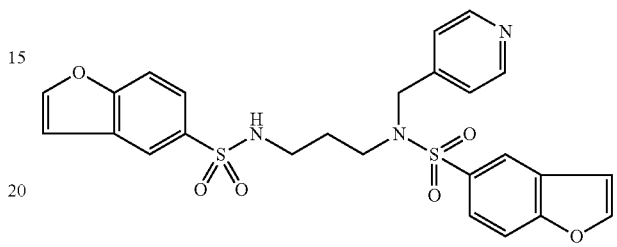
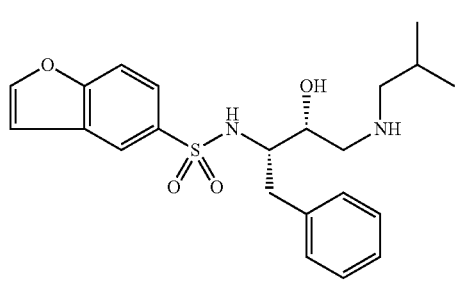
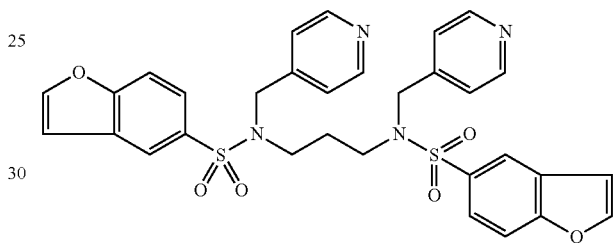
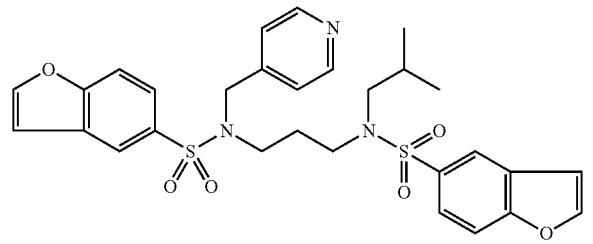
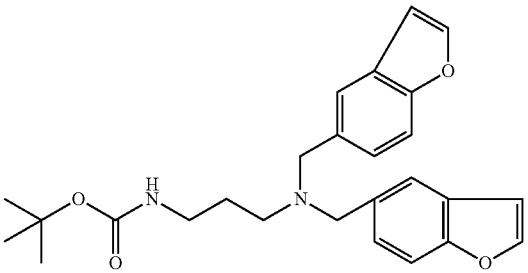
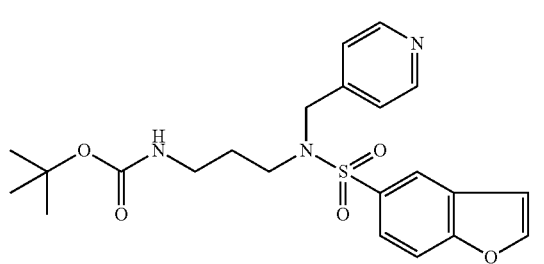
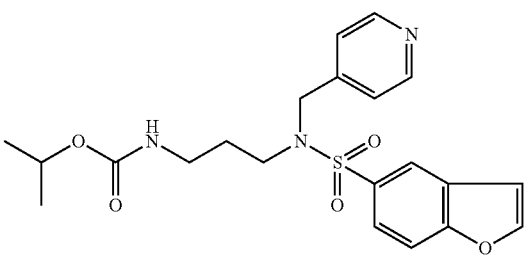
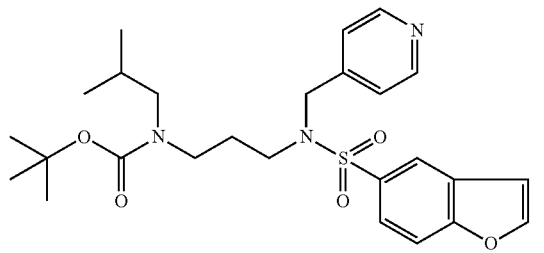
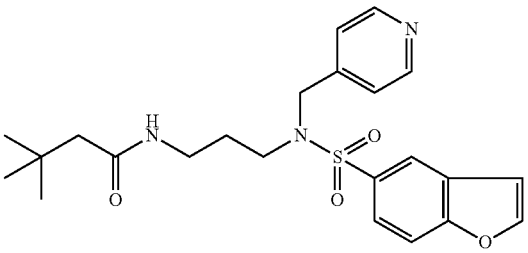

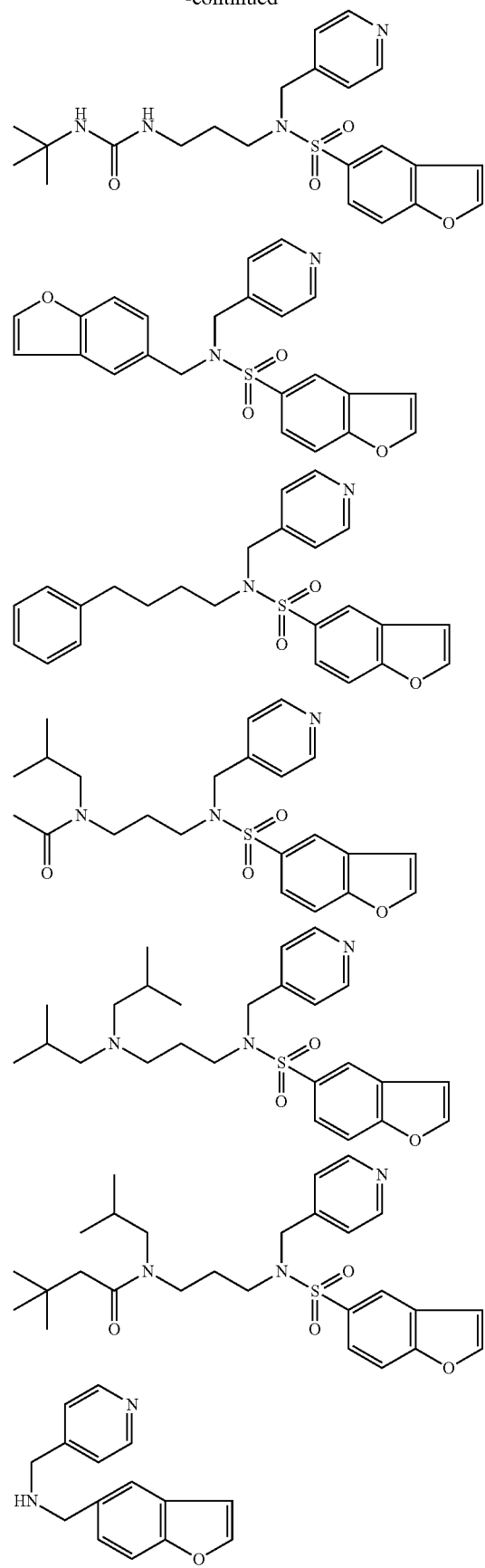
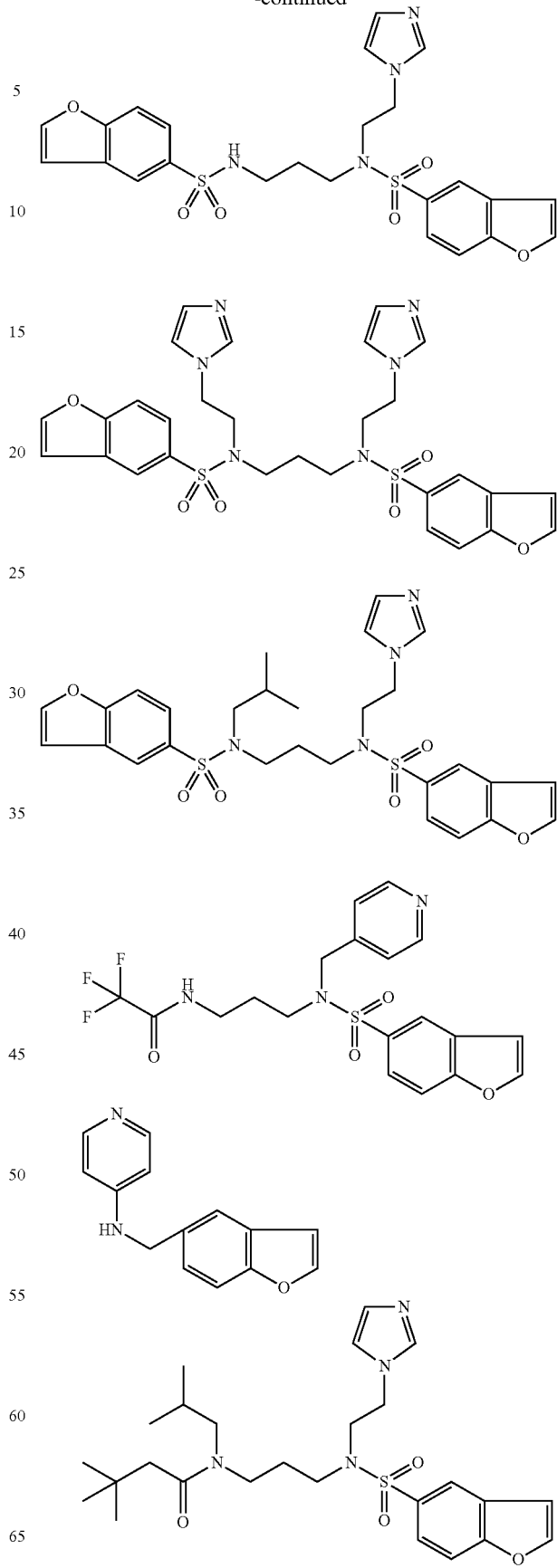

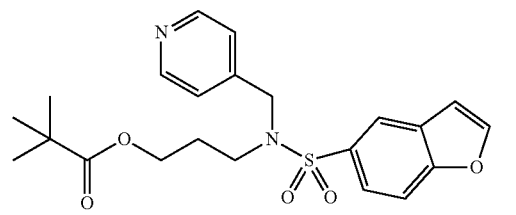
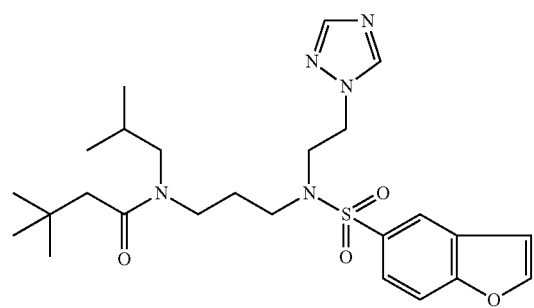
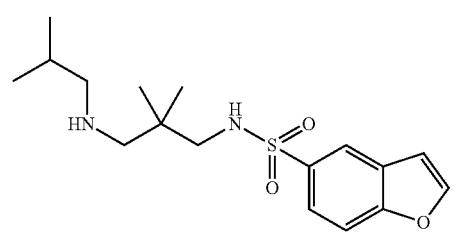
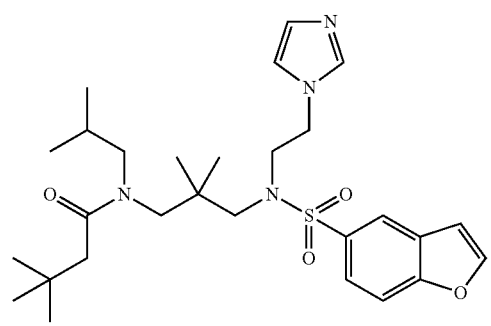
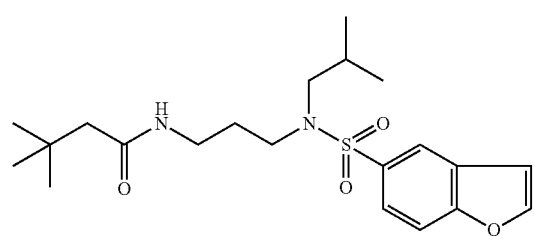
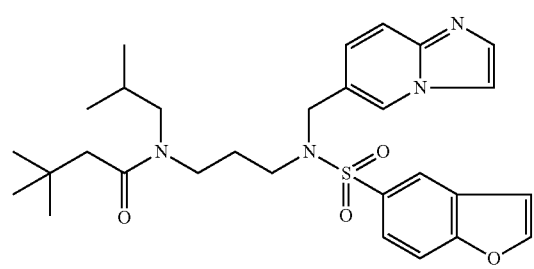
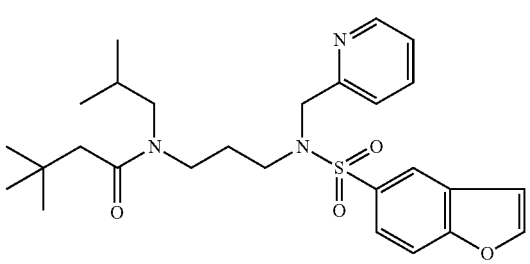
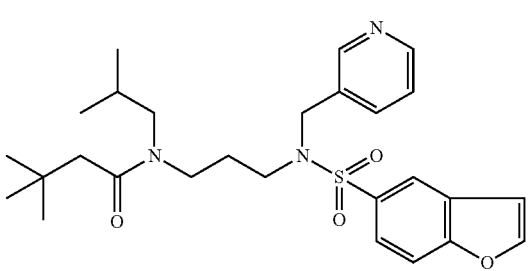
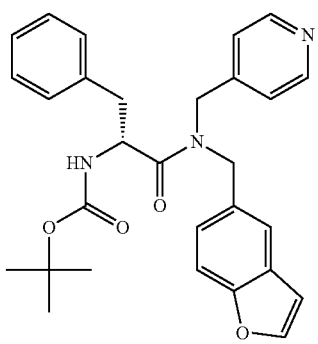
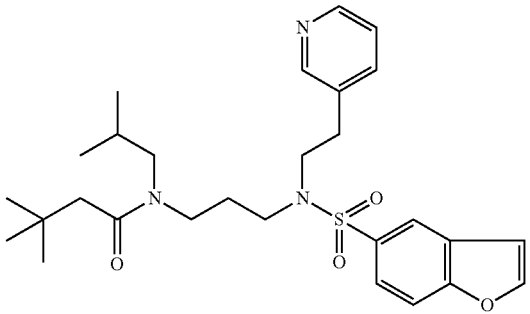
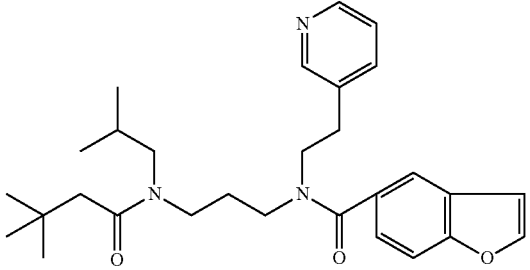

-continued

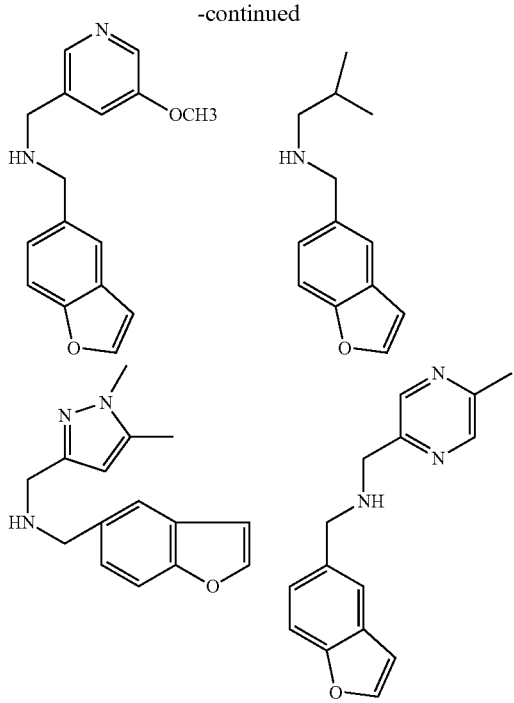

The term "pharmaceutically effective amount" or "therapeutically effective amount" or "therapeutic dose" or "efficacious dose" refers to an amount that when administered to a subject is effective in inhibiting cytochrome P450 enough to reduce or prevent the in vivo degradation of a co-administered drug and thereby improve the pharmacokinetics of the drug and/or boost its efficacy. The term "treating" as used herein refers to the alleviation of symptoms of a particular disorder in a subject, such as a human patient, or the improvement of an ascertainable measurement associated with a particular disorder. The term "prophylactically effective amount" refers to an amount effective in preventing a disease in a subject, such as a human patient. As used herein, a "subject" refers to a mammal, including a human.

The term "substituted", whether preceded by the term "optionally" or not, and substitutions contained in formulas of this invention, include the replacement of one or more hydrogen radicals in a given structure with the radical of a specified substituent. When more than one position in a given structure can be substituted with more than one substituent selected from a specified group, the substituents can be either the same or different at every position (for example, in the moiety —N(R2)(R2), the two R2 substituents can be the same or different). Typically, when a structure can be optionally substituted, 0-3 substitutions are preferred, and 0-1 substitution is more preferred. Advantageously, each substituent enhances cytochrome P450 inhibitory activity in permissive mammalian cells, or enhances deliverability by improving solubility characteristics or pharmacokinetic or pharmacodynamic profiles as compared to the unsubstituted compound. Combinations of substituents and variables envisioned by this invention are limited to those that result in the formation of stable compounds.

The term "stable", as used herein, refers to compounds which possess stability sufficient to allow manufacture, formulation, and administration to a mammal by methods known in the art. Typically, such compounds are stable at a temperature of 40° C. or less, in the absence of moisture or other chemically reactive conditions, for at least a week.

The term "alkyl", alone or in combination with any other term, refers to a straight-chain or branched-chain saturated aliphatic hydrocarbon radical containing the specified number of carbon atoms, or where no number is specified, advantageously from 1 to about 12 or 1 to 15 carbon atoms. Examples of alkyl radicals include, but are not limited to: methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, advantageously from 2-6 or 2-10 carbon atoms. Alkenyl groups include all possible E and Z isomers unless specifically stated otherwise. Examples of alkenyl radicals include, but are not limited to, ethenyl, propenyl, isopropenyl, butenyl, isobutenyl, pentenyl, hexenyl, hexadienyl and the like.

The term "alkynyl," alone or in combination with any other term, refers to a straight-chain or branched-chain hydrocarbon radical having one or more triple bonds containing the specified number of carbon atoms, or where no number is specified, advantageously from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, where the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The terms "alkylamino" or "dialkylamino" include amino radicals substituted by one or two alkyl groups, where the term "alkyl" is defined above, and the alkyl group can be the same or different. Examples of suitable alkylamino and dialkylamino radicals include, but are not limited to, methylamino, ethylamino, isoproylamino, dimethylamino, methylethylamino, ethylbutylamino and the like.

The term "hydroxyalkyl" refers to an alkyl radical as defined above in which one of the hydrogen atoms is replaced by hydroxy group. Examples of suitable hydroxyalkyl radicals include, but are not limited to, hydroxymethyl, 2-hydroxypropyl and the like.

The term "alkoxyalkyl" refers to an alkyl radical as defined above in which one of the hydrogen atoms is replaced by an alkoxy radical as defined above.

The terms "aminoalkyl", "alkylaminoalkyl" or "dialkylaminoalkyl" refers to an alkyl radical as defined above in which one of the hydrogen atoms is replaced by an amino or "alkylamino" or "dialkylamino" radical as defined above.

The term "halo" or "halogen" includes fluorine, chlorine, bromine or iodine.

The term "haloalkyl" includes alkyl groups with one or more of its hydrogens replaced by halogens.

The term "thioalkyl" includes alkyl radicals having at least one sulfur atom, where alkyl has the significance given above. An example of a thioalkyl is $CH_3SCH_2$. The definition also encompasses the corresponding sulfoxide and sulfone of this thioalkyl $CH_3S(O)CH_2$ and $CH_3S(O)_2CH_2$ respectively. Unless expressly stated to the contrary, the terms "—$SO_2$—" and "—$S(O)_2$—" as used herein include sulfone or sulfone derivative (i.e., both appended groups linked to the S), and not a sulfinate ester.

The terms "carboalkoxy" or "alkoxycarbonyl" include alkyl esters of a carboxylic acid. Examples of "carboalkoxy" or "alkoxycarbonyl" radicals include, but are not limited to ethoxycarbonyl (or carboethoxy), Boc (or t-butoxycarbonyl), Cbz (or benzyloxycarbonyl) and the like.

The term "alkanoyl" includes acyl radicals derived from an alkanecarboxylic acid. Examples of alkanoyl radicals include, but are not limited to acetyl, propionyl, isobutyryl and the like.

The term "aryl," alone or in combination with any other term, refers to a carbocyclic aromatic radical (such as phenyl or naphthyl) containing the specified number of carbon atoms, preferably from 6-15 carbon atoms, and more preferably from 6-10 carbon atoms, optionally substituted with one or more substituents selected from alkyl, alkoxy, (for example methoxy), nitro, halo, amino, mono or dialkylamino, carboalkoxy, cyano, thioalkyl, alkanoyl, carboxylate, and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, includes alkyl radicals as defined above in which one or more hydrogen atoms is replaced by an aryl radical as defined above. Examples of aralkyl radicals include, but are not limited to benzyl, 2-phenylethyl and the like.

The term "aralkanoyl" includes acyl radicals derived from an aryl-substituted alkanecarboxylic acid such as phenylacetyl, 3-phenyipropionyl (hydrocinnamoyl), 4-phenylbutyryl, (2-naphthyl)acetyl, 4-chlorohydrocinnamoyl, 4-aminohydrocinnamoyl, (1-naphthyl)acetyl, 4-methoxyhydrocinnamoyl, and the like.

The term "aroyl" includes acyl radicals derived from an aromatic carboxylic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "arylsulfonyl" includes sulfonyl radicals derived from an aromatic sulfonic acid such as benzenesulfonyl, 4-chlorobenzenesulfonyl, 1-naphthalenesulfonyl, 2-naphthalenesulfonyl, and the like.

The term "carbocycle" refers to a non-aromatic stable 3- to 8-membered carbon ring which can be saturated, monounsaturated or poly-unsaturated. The carbocycle can be attached at any endocyclic carbon atom which results in a stable structure. Preferred carbocycles have 5-7 carbons.

The term "cycloalkyl", alone or in combination, includes alkyl radicals which contain from about 3 to about 8 carbon atoms and are cyclic. Examples of such cycloalkyl radicals include cyclopropyl, cyclobutyl, cyclopentyl, cyclohexyl and the like.

The term "cycloalkenyl" alone or in combination includes alkenyl radicals as defined above which contain about 3-8 carbon atoms and are cyclic.

The term "cycloalkylalkyl" includes alkyl radicals as defined above which are substituted by a cycloalkyl radical containing from about 3 to about 8, preferably from about 3 to about 6, carbon atoms.

The term "heterocyclyl" or "heterocyclo" or "heterocycloalkyl" refers to a stable 3-7 membered monocyclic heterocycle or 8-11 membered bicyclic heterocycle which is either saturated or partially unsaturated, and which can be optionally benzofused if monocyclic and which is optionally substituted on one or more carbon atoms by halogen, alkyl, alkoxy, oxo, and the like, and/or on a secondary nitrogen atom (i.e., –NH—) by alkyl, aralkoxycarbonyl, alkanoyl, phenyl or phenylalkyl or on a tertiary nitrogen atom (i.e., +N—) by oxido and which is attached via a carbon atom.

Each heterocycle consists of one or more carbon atoms and from one to four heteroatoms selected from the group consisting of nitrogen, oxygen and sulfur. As used herein, the terms "nitrogen and sulfur heteroatoms" include oxidized forms of nitrogen and sulfur, and the quaternized form of any basic nitrogen. A heterocyclyl radical can be attached at any endocyclic carbon or heteroatom which results in the creation of a stable structure. Preferred heterocycles include 5-7 membered monocyclic heterocycles, and 8-10 membered bicyclic heterocycles. Examples of such groups imidazolinyl, imidazolidinyl, indazolinyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroaryl" refers to stable 5-6 membered monocyclic or 8-11 membered bicyclic or 13-16 membered tricyclic aromatic heterocycles where heterocycles is as defined above. Non-limiting examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiazolyl, thiadiazyl, oxathiolyl, acridinyl, phenanthridinyl, and benzocinnolinyl.

The term "heterocycloalkylalkyl" refers to an alkyl radical as defined above which is substituted by a heterocycloalkyl radical as defined above.

The term "heteroaralkyl" alone or in combination, includes alkyl radicals as defined above in which one or more hydrogen atom is replaced by a hetoroaryl group as defined above.

As used herein, the compounds of this invention are defined to include pharmaceutically acceptable derivatives or prodrugs thereof. A "pharmaceutically acceptable derivative or prodrug" includes a pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Examples of prodrugs of hydroxy containing compounds are amino acid esters or phosphonate or phosphate esters that can be cleaved in vivo hydrolytically or enzymatically to provide the parent compound. These have the advantage of providing potentially improved solubility.

The compounds of this invention can contain one or more asymmetric carbon atoms and thus occur as racemates and racemic mixtures, single enantiomers, diastereomeric mixtures and individual diastereomers. All such isomeric forms of these compounds are expressly included in the invention. Each stereogenic carbon can be of the R or S configuration. Although the specific compounds exemplified in this application can be depicted in a particular stereochemical configuration, compounds having either the opposite stereochemistry at any given chiral center or mixtures thereof are also envisioned.

Preparation of the Compounds

The compounds can be prepared according to synthetic methods known in the art. For example, benzofuran sulfonamides may be prepared by coupling of an amine to a benzofuranyl sulfonyl chloride. In other examples, basic amine compounds of the invention may be prepared by reductive amination reactions in which an amine and an aldehyde are reacted to form a Schiff's base, which is reduced with, for example, sodium borohydride, to form the desited amine. Other synthetic methods that can be used to prepare the subject compounds are set forth, for example, in U.S. Pat. No. 6,319,946 to Hale et al., and in *J.Med.Chem.* 36, 288-291 (93), the disclosures of which are incorporated herein by reference in their entireties, together with procedures of the type described below.

Specific examples of syntheses of compounds of the invention include:

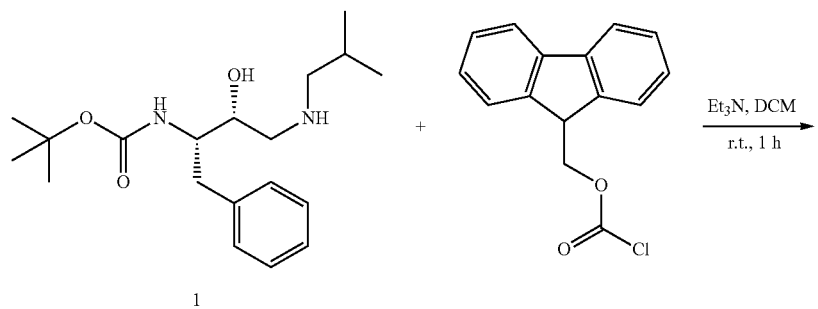

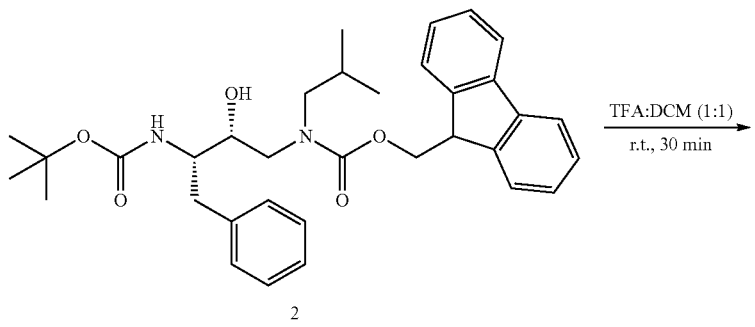

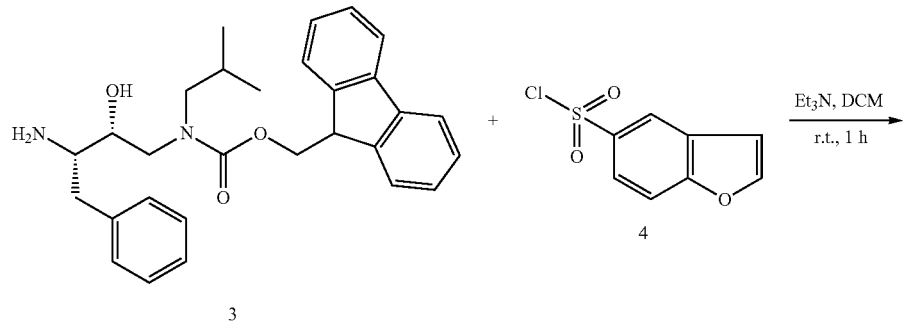

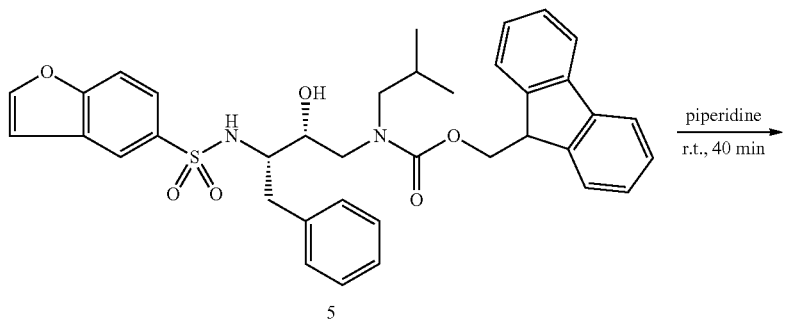

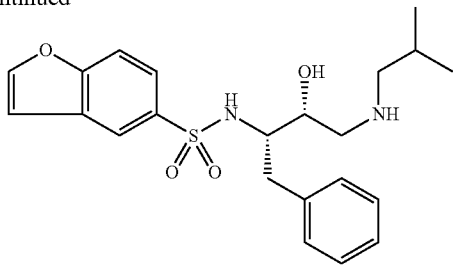

6

In this example, the secondary amino group of compound 1 is protected as an FMOC derivative, followed by deprotection of the primary amino group to give compound 3, which then is reacted with the benzofuran sulfonyl chloride 4 to give compound 5. Removal of the FMOC group with a base such as piperidine provides compound 6.

Another example is:

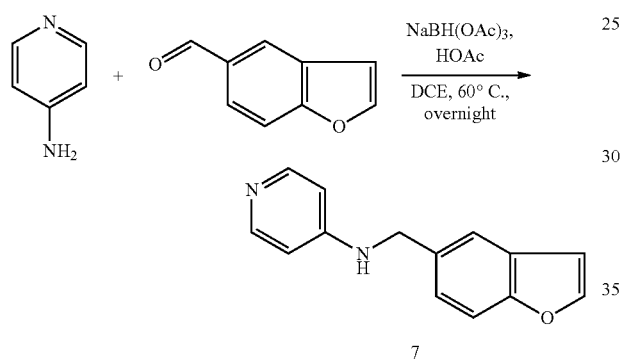

7

Here, the benzofuranyl aldehyde and the pyridyl amine are coupled via a reductive amination reaction to provide compound 7.

A further example is:

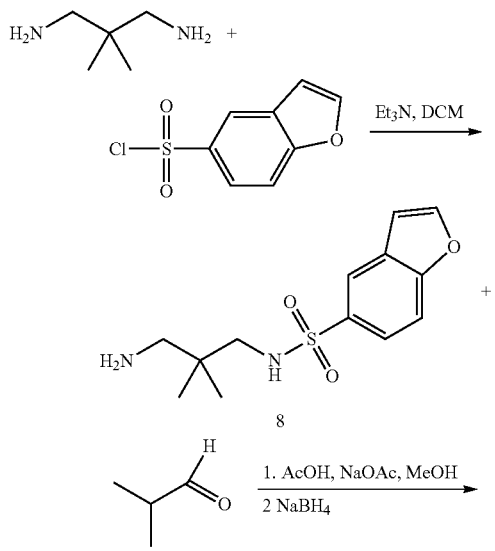

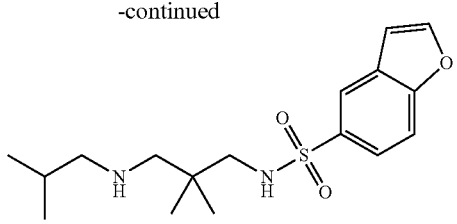

9

The dimethylpropanediamine is reacted with the benzofuran sulfonyl chloride to provide compound 8, which is reductively coupled with isobutyraldehyde to provide compound 9.

Use of Compounds for "Boosting"

Cytochrome P450 2D6 enzymes are responsible for the metabolic degradation of a variety of drug molecules, thus disturbing their pharmacokinetics and reducing their bioavailabilty. Compositions that can inhibit cytochrome P450 can therefore improve the pharmacokinetics and bioavailability of such drugs.

In certain embodiments, there are provided methods for inhibiting cytochrome P450 monooxygenase by administering to a patient, one or more compounds described herein. The compound can function as a potent cytochrome P450 2D6 inhibitor and can improve the pharmacokinetics of a drug (or a pharmaceutically acceptable salt thereof) which is metabolized by cytochrome P450 2D6. The compound or its pharmaceutically acceptable salt can be administered by itself or in combination with the other drug. When administered in combination, the two therapeutic agents can be formulated as separate compositions which are administered at the same time or different times, or the two therapeutic agents can be administered as a single composition.

The compounds described above are effective for inhibiting a CYP 2D6 enzyme. Use of the compounds of the invention therefore permits reduced rates of drug degradation and extended durations of action in vivo. The compounds are useful for "boosting" the activity of a variety of drugs.

Methods of Administration of Compounds

The compounds of the invention can be administered in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Other pharmaceutically acceptable salts include salts with an inorganic base, organic base, inorganic acid, organic acid, or basic or acidic amino acid. Inorganic bases which form the pharmaceutically acceptable salts include alkali metals such as sodium or potassium, alkali earth metals such as calcium and magnesium, aluminum, and ammonia. Organic bases which form pharmaceutically acceptable salts include trimethylamine, triethylamine, pyridine, picoline, ethanolamine, diethanolamine, triethanolamine, dicyclohexylamine. Inorganic acids which form the pharmaceutically acceptable salts include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

Also contemplated are compositions which can be administered orally or non-orally in the form of, for example, granules, powders, tablets, capsules, syrup, suppositories, injections, emulsions, elixirs, suspensions or solutions, by mixing these effective components, individually or simultaneously, with pharmaceutically acceptable carriers, excipients, binders, diluents or the like.

As a solid formulation for oral administration, the composition can be in the form of powders, granules, tablets, pills and capsules. In these cases, the compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. The formulations can contain further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

Examples of liquid preparations for oral administration include pharmaceutically acceptable emulsions, syrups, elixirs, suspensions and solutions, which can contain an inactive diluent, for example, water.

As used herein, "non-orally" includes subcutaneous injection, intravenous injection, intramuscular injection, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections can be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides. The pharmaceutical compositions can be formulated for nasal aerosol or inhalation and can be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

The pharmaceutical composition can be formulated for topical administration with a suitable ointment containing one or more of the compounds suspended or dissolved in a carrier, which include mineral oil, liquid petroleum, white petroleum, propylene glycol, polyoxyethylene, polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetaryl alcohol, 2-octyldodecanol, benzyl alcohol and water.

In some embodiments, the pharmaceutical compositions can include α-, β-, or γ-cyclodextrins or their derivatives. In certain embodiments, co-solvents such as alcohols can improve the solubility and/or the stability of the compounds in pharmaceutical compositions. In the preparation of aqueous compositions, addition salts of the compounds can be suitable due to their increased water solubility.

Appropriate cyclodextrins are α-, β-, or γ-cyclodextrins (CDs) or ethers and mixed ethers thereof where one or more of the hydroxy groups of the anhydroglucose units of the cyclodextrin are substituted with $C_1$-$C_6$alkyl, such as methyl, ethyl or isopropyl, e.g. randomly methylated β-CD; hydroxy $C_{16}$ alkyl, particularly hydroxy-ethyl, hydroxypropyl or hydroxybutyl; carboxy $C_1$-$C_6$alkyl, particularly carboxymethyl or carboxyethyl; $C_1$-$C_6$alkyl-carbonyl, particularly acetyl; $C_1$-$C_6$ alkyloxycarbonyl$C_1$-$C_6$alkyl or carboxy$C_1$-$C_6$alkyloxy$C_1$-$C_6$alkyl, particularly carboxymethoxypropyl or carboxyethoxypropyl; $C_1$-$C_6$alkylcarbonyloxy$C_1$-$C_6$alkyl, particularly 2-acetyloxypropyl. Complexants and/or solubilizers are β-CD, randomly methylated β-CD, 2,6-dimethyl-β-CD, 2-hydroxyethyl-β-CD, 2-hydroxyethyl-γ-CD, hydroxy-propyl-γ-CD and (2-carboxymethoxy)propyl-β-CD, and 2-hydroxy-propyl-β-CD (2-HP-β-CD) can be used.

The term "mixed ether" denotes cyclodextrin derivatives where at least two cyclodextrin hydroxy groups are etherified with different groups such as, for example, hydroxy-propyl and hydroxyethyl.

The compounds can be formulated in combination with a cyclodextrin or a derivative thereof as described in U.S. Pat. No. 5,707,975. Although the formulations described therein are with antifungal active ingredients, they are equally relevant for formulating compounds as described herein. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations can also be rendered more palatable by adding pharmaceutically acceptable sweeteners and/or flavors.

Other methods to enhance the solubility of the compounds described herein in pharmaceutical compositions are described in WO 94/05263, WO 98/42318, EP-A-499,299 and WO 97/44014, all incorporated herein by reference.

In some embodiments, the compounds can be formulated in a pharmaceutical composition comprising a therapeutically effective amount of particles consisting of a solid dispersion comprising a compound of formula I, and one or more pharmaceutically acceptable water-soluble polymers.

The term "solid dispersion" defines a system in a solid state comprising at least two components, where one component is dispersed more or less evenly throughout the other component or components. When the dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "solid dispersion" also includes dispersions which are less homogenous throughout than solid solutions. Such dispersions are not chemically and physically uniform throughout or comprise more than one phase.

The water-soluble polymer in the particles can be a polymer that has an apparent viscosity of 1 to 100 mPa·s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

The compounds can be formulated in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The compounds can also be incorporated in hydrophilic polymers and applied as a film over many small beads, thus yielding a composition with good bioavailability which can be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration can depend on the condition of the subject, co-medication and the like.

Dosages of the compounds can depend on age, body weight, general health conditions, sex, diet, dose interval, administration routes, excretion rate, combinations of drugs and conditions of the diseases treated, while taking these and other necessary factors into consideration. Generally, dosage levels of between about 10 μg per day to about 5000 mg per day, preferably between about 10 mg per day to about 1000 mg per day of the compound are useful for the inhibition of CYP 2D6 enzymes. Typically, the pharmaceutical compositions of this invention will be administered from about 1 to about 3 times per day or alternatively, as a continuous infusion. Such administration can be used as a chronic or acute therapy.

The amount of active ingredient that can be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 5% to about 95% active compound (w/w). Preferably, such preparations contain from about 10% to about 80% active compound. The desired unit dose of a composition of this invention is administered once or multiple times daily.

In some embodiments, the invention contemplates compositions and formulations comprising one or more of the compounds in combination with one or more other drugs that can be metabolized or degraded by CYP 2D6.

The CYP inhibitors of this invention can be administered to a patient either as a single agent (for use with a separate dose of another drug) or in a combined dosage form with at least one other drug. Additional drugs also can be used to increase the therapeutic effect of these compounds.

Cyp inhibitors can also be used as standalone therapeutics for Cyp-mediated diseases, or as prophylactic agents for preventing the production of toxic metabolites.

Such combination therapy in different formulations can be administered simultaneously, separately or sequentially. The Cyp inhibitors can be administered prior to administration of the other drug to reduce Cyp levels and minimize degradation of the drug. In specific embodiments, the Cyp inhibitor is administered, 30 minutes, 1 hour, four hours, twelve hours or twenty four hours prior to initial administration of the other drug. The Cyp inhibitors tend to have a long half-life in vivo, presumably as a result of inhibiting their own metabolism. This means that once treatment has begun, the Cyp inhibitor may be administered less frequently than the drug, although the skilled artisan will recognize that different administration regiments may be needed in specific situations. Alternatively, such combinations can be administered as a single formulation, whereby the active ingredients are released from the formulation simultaneously or separately.

The following examples illustrate further the invention but, of course, should not be construed in any way of limiting its scope.

EXAMPLES

Example 1

Synthetic Methods

The following experimental protocols are illustrative of the methods used to synthesize compounds of the invention. Syntheses of the compounds below are exemplified, although the skilled artisan will recognize that these exemplary methods are of general applicability.

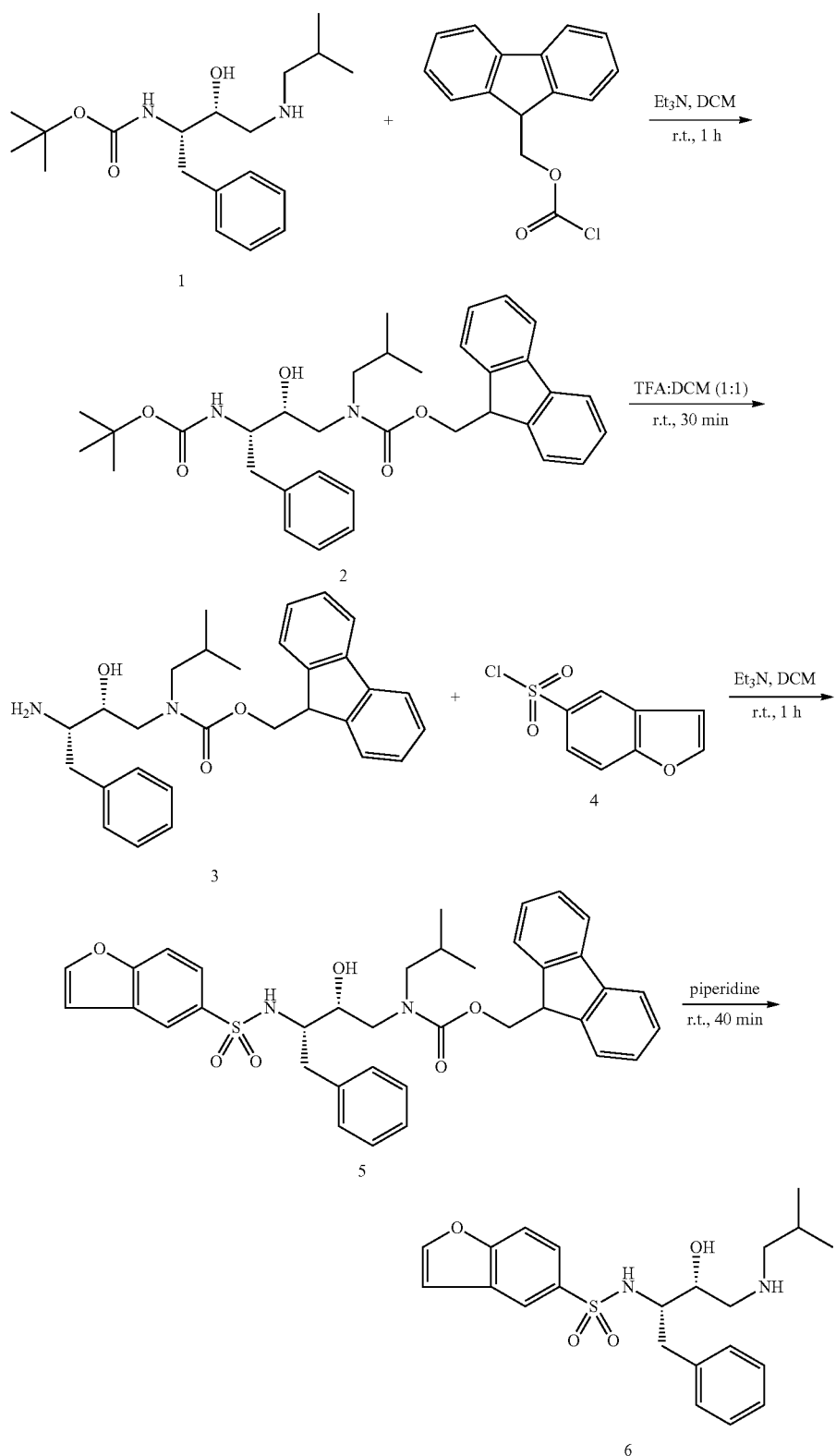

(1-Benzyl-2-hydroxy-3-isobutylamine-propyl)-carbamic acid tert-butyl ester 1 (1006 mg, 3.0 mmol, 1.0 equiv.) and Fmoc chloride (854 mg, 3.3 mmol, 1.1 equiv.) were dissolved in dichloromethane (15 mL). To the solution was added triethylamine (502 μL, 3.6 mmol, 1.2 equiv.) at room temperature. The mixture was stirred at the same temperature for 1 h, after which time the reaction was quenched through the addition of a small amount of silica gel and dichloromethane. The mixture was concentrated in vacuo and the residue was purified by MPLC on silica gel (ethyl acetate in hexane, 0-100%) to afford the target 2 as a white solid (1270 mg, 76%). Mass 581 (MNa)+, and 459 (M-Boc)−. Purity 99% (HPLC).

To the solution of 2 (260 mg, 0.47 mmol, 1.0 equiv.) in dichloromethane (0.3 mL) was added trifluoroacetic acid (0.3 mL) at 0° C. Then the mixture was stirred at room temperature for 30 min, after which time the solution was diluted with dichloromethane (20 mL) and saturated NaHCO$_3$ solution (10 mL) and the two layers separated. The organic phase was washed twice with brine, dried over Na$_2$SO$_4$, and concentrated in vacuo to afford the crude product 3, which was used directly in the next step.

To a solution of 3 (210 mg, 0.46 mmol, 1.0 equiv.) in dichloromethane (2 mL) was added Benzofuran-5-sulfonyl chloride (4) (109 mg, 0.50 mmol, 1.1 equiv.) and triethylamine (77 μL, 0.55 mmol, 1.2 equiv.). The mixture was stirred at room temperature for 60 min and a small amount of silica gel was added. Then the solution was concentrated in vacuo. The residue was purified by MPLC on silica gel (ethyl acetate in hexane, 0-60%) to afford the target 5 as a white solid (220 mg, 75%). Mass 639 (MH)+, and 415 (M-FmocH)−. Purity 98% (HPLC).

A solution of 5 in piperidine (2.4 mL) was stirred at room temperature for 60 min and poured into 20 mL of cold water. The solution was extracted with ethyl acetate. The combined organic phase was dried over Na$_2$SO$_4$ and concentrated in vacuo. The residue was purified by flash column chromatography (ethyl acetate/dichloromethane/methanol 5:5:1) to afford the target 6 as an oil (72 mg, 72%). Mass 417 (MH)+, 451 (MCl)−, 415 (M-H)−. Purity 99% (HPLC).

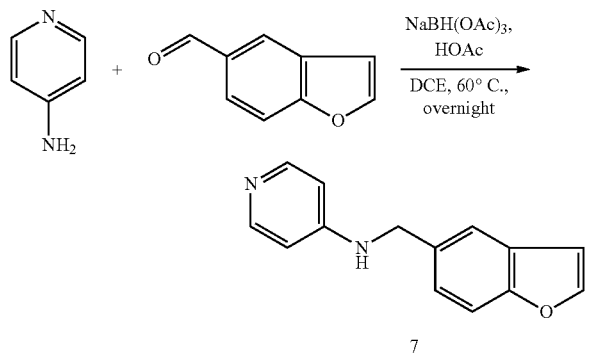

Benzofuran-5-carbaldehyde (330 mg, 2.19 mmol, 1.0 equiv.) and 4-aminopyridine (227 mg, 2.41 mmol, 1.1 equiv.) were combined in 1,2-dichloroethane (22 mL) and treated with acetic acid (138 uL, 2.41 mmol, 1.1 equiv.) and sodium triacetoxyborohydride (969 mg, 4.34 mmol, 1.98 equiv.). The mixture was stirred at 60° C. overnight, and then quenched by addition of saturated NaHCO$_3$ solution. The two phases were separated and the water layer was extracted twice with ethyl acetate. The combined organic phase was dried over Na$_2$SO$_4$, filtered and concentrated in vacuo. The residue was purified with flash column chromatography on silica gel, eluting with ethyl acetate/dichloromethane/methanol to afford the target 7 as a white solid (62 mg, 13%). Mass: 225 (MH)+. Purity >99% (HPLC).

To a solution of 2,2-dimethylpropane-1,3-diamine (2.0 g, 19.6 mmol) in dichloromethane (20 ml) were added triethylamine (4.0 ml, 29.4 mmol) and benzofuran-5-sulfonyl chloride (4.2 g, 19.6 mmol). The mixture was stirred for 10 min at room temperature, quenched with saturated sodium bicarbonate aqueous solution (20 ml), and extracted with dichloromethane (10 ml). The organic phase was washed with brine (30 ml), dried over MgSO$_4$, and concentrated in vacuo. MPLC on silica gel (dichloromethane→30% methanol in dichloromethane) afforded 8 (4.2 g, 76%) as a white solid.

To a solution of 8 (1.0 g, 3.5 mmol) in methanol (15 ml) were added isobutyraldehyde (702 μl, 7.7 mmol), acetic acid (440 μl, 7.7 mmol) and sodium acetate (631 mg, 7.7 mmol). The mixture was stirred for 30 min at rt and treated with sodium borohydride (529 mg, 14.0 mmol). After 30 min, sodium bicarbonate (aq) (20 ml) was added to quench the reaction. The water phase was extracted with ethyl acetate (15 ml) and the organic layer was washed with brine (20 ml), dried over magnesium sulfate and concentrated in vacuo. MPLC on silica gel (hexanes→ethyl acetate) afforded 9 (690 mg, 68%) as a white solid. Mass 339 [MH]+, purity: 99% (HPLC).

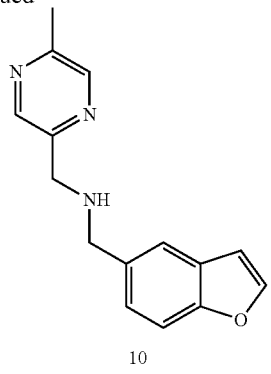

To solution of 2-(Aminomethyl)-5-methylpyrazine (65 mg, 0.53 mmol) in methanol (4 ml) were added benzofuran-5-carbaldehyde (77 mg, 0.53 mmol), acetic acid (33 μl, 0.58 mmol) and sodium acetate (48 mg, 0.58 mmol). The mixture was stirred for 30 min at rt and treated with sodium borohydride (40 mg, 1.06 mmol). After 30 min, sodium bicarbonate (aq) (8 ml) was added to quench the reaction. The aqueous phase was extracted with ethyl acetate (10 ml) and the organic layer was washed with brine (10 ml), dried over magnesium sulfate and concentrated in vacuo. Preparative thin layer chromatography (dichloromethane:methanol=10:1) afforded 10 (102 mg, 75%) as a yellow oil. Mass 254 [MH]$^+$, purity: 100% (HPLC).

Variations, modifications, and other implementations of what is described herein will occur to those of ordinary skill in the art without departing from the spirit and the scope of the invention. Accordingly, the invention is not to be limited only to the preceding illustrative descriptions.

What is claimed is:

1. A method of inhibiting a cytochrome P450 2D6 enzyme comprising contacting said enzyme with a compound comprising a benzofuran moiety attached on its benzene ring via a linker to a basic amino group or a salt form thereof.

2. The method of claim 1 wherein the linker is at the 5-position of the benzofuran moiety.

3. The method of claim 1 wherein the basic amino group is a secondary or tertiary amine.

4. The method according to claim 2, wherein said compound has the structure:

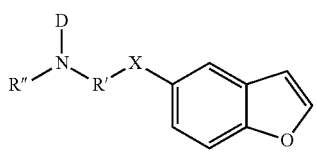

wherein: X is [—N(D)-SO$_n$—]$_q$, wherein n is 1 or 2 and q is 0 or 1;
R' is C$_1$-C$_6$ alkyl when q is 0, or C$_2$-C$_6$ alkyl when q is 1, wherein R' optionally is substituted by up to 3 substituents independently selected from the group consisting of C$_1$-C$_3$ alkyl, OH, O-alkyl, alkylamido, alkylcarbamoyl, halo, nitro, cyano, S-alkyl, aralkyl and heteroaralkyl;
each D independently is selected from the group consisting of hydrogen, alkyl, cycloalkyl, cycloalkylalkyl, heterocycloalkyl, heterocycloalkylalkyl, aryl, heteroaryl, heteroaralkyl and aralkyl;
R" is C$_1$-C$_6$ alkyl, C$_3$-C$_6$ cycloalkyl, C$_3$-C$_6$ cycloalkyl-C$_1$-C$_6$-alkyl, heterocycloalkyl, heterocycloalkylalkyl, aryl, heteroaryl, heteroaralkyl or aralkyl, optionally substituted by up to 3 substituents independently selected from the group consisting of OH, O-alkyl, alkylamido, alkylcarbamoyl, halo, nitro, cyano, S-alkyl, aralkyl and heteroaralkyl.

5. The method of claim 4 wherein said compound is selected from the group consisting of:

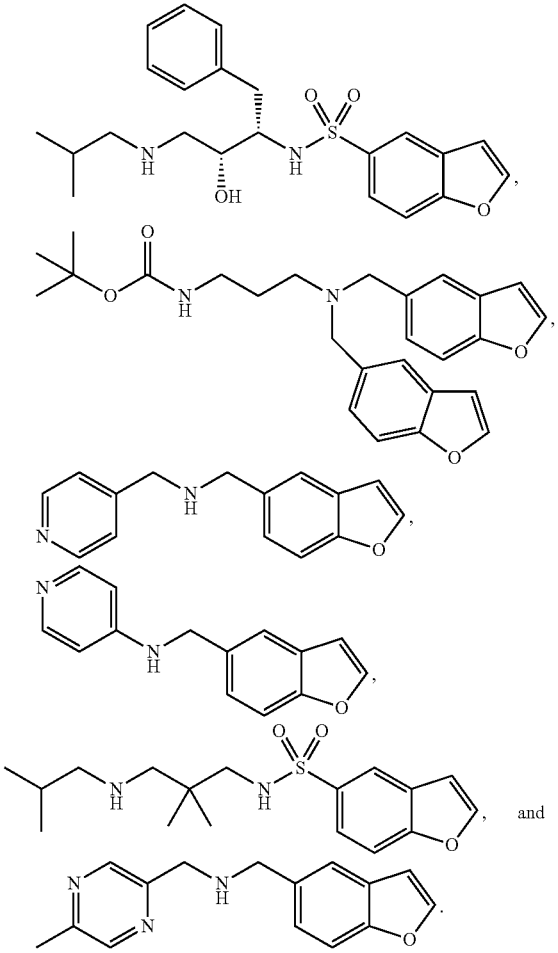

6. The method according to claim 1, wherein said cytochrome P450 2D6 enzyme is in a subject.

7. The method of claim 6 wherein the linker is at the 5-position of the benzofuran moiety.

8. The method of claim 6 wherein the basic amino group is a secondary or tertiary amine.

9. The method according claim 6, further comprising administering the compound prior to or substantially contemporaneously with a drug, wherein efficacy of said drug is compromised due to degradation by cytochrome P450 2D6 enzyme.

10. The method of claim 9 wherein said drug is dextromethorphan.

* * * * *